United States Patent [19]

Lantzsch et al.

[11] Patent Number: 4,596,880
[45] Date of Patent: Jun. 24, 1986

[54] COMBATING ARTHROPODS WITH NOVEL BENZYL ESTERS

[75] Inventors: Reinhard Lantzsch; Albrecht Marhold, both of Leverkusen; Wolfgang Behrenz, Overath; Ingeborg Hammann, Cologne, all of Fed. Rep. of Germany

[73] Assignee: Bayer Aktiengesellschaft, Leverkusen, Fed. Rep. of Germany

[21] Appl. No.: 548,123

[22] Filed: Nov. 2, 1983

Related U.S. Application Data

[62] Division of Ser. No. 288,440, Jul. 30, 1981, Pat. No. 4,438,275, which is a division of Ser. No. 30,579, Apr. 16, 1979, Pat. No. 4,310,540.

[30] Foreign Application Priority Data

May 5, 1978 [DE] Fed. Rep. of Germany ....... 2819788

[51] Int. Cl.$^4$ .......................................... C07D 319/14
[52] U.S. Cl. .................................... 549/362; 549/366
[58] Field of Search .......................................... 549/362

[56] References Cited

U.S. PATENT DOCUMENTS

| | | | |
|---|---|---|---|
| 886,085 | 4/1908 | Stalmann | 549/436 |
| 3,378,592 | 4/1968 | Lutz | 549/434 |
| 3,673,237 | 6/1972 | Janiak | 560/124 |
| 3,792,079 | 2/1974 | D'Orazio | 560/124 |
| 3,793,036 | 8/1976 | Hirano et al. | 424/304 |
| 3,979,519 | 9/1976 | Punja | 560/124 |
| 4,002,769 | 1/1977 | Schwarz | 424/282 |
| 4,003,945 | 1/1977 | Kitamura et al. | 260/340.5 R |
| 4,078,080 | 3/1978 | Schrider | 424/304 X |
| 4,083,863 | 4/1978 | Brand | 560/21 |
| 4,100,297 | 7/1978 | Grandadam et al. | 424/304 |
| 4,105,780 | 8/1978 | Berkelhammer et al. | 260/340.5 R |
| 4,110,345 | 8/1978 | Berkelhammer et al. | 549/434 |
| 4,137,324 | 1/1979 | Elliott et al. | 424/308 X |
| 4,157,447 | 6/1979 | Engel | 424/308 X |
| 4,166,064 | 8/1979 | Kondo et al. | 560/124 |
| 4,179,518 | 12/1979 | Felton et al. | 424/300 |
| 4,182,772 | 1/1980 | Badmin et al. | 424/304 |
| 4,183,861 | 1/1980 | Maggioni | 549/436 |
| 4,183,948 | 1/1980 | Huff | 424/304 |
| 4,183,950 | 1/1980 | Naumann et al. | 424/305 |
| 4,194,001 | 3/1980 | Ruscoe et al. | 424/304 |
| 4,199,595 | 4/1980 | Berkelhammer et al. | 260/465 D |
| 4,199,596 | 4/1980 | Fuchs et al. | 424/282 |
| 4,214,004 | 7/1980 | Plummer | 424/305 |
| 4,217,300 | 8/1980 | Lantzsch | 260/465 D |
| 4,217,302 | 8/1980 | Anderson et al. | 549/362 |
| 4,218,469 | 8/1980 | Fuchs et al. | 424/304 |
| 4,219,564 | 8/1980 | Drabek et al. | 560/124 |
| 4,294,762 | 10/1981 | Hoffmann | 549/362 |

FOREIGN PATENT DOCUMENTS

| | | | |
|---|---|---|---|
| 0035003 | 3/1980 | Japan | 549/436 |
| 1159089 | 7/1969 | United Kingdom | 549/445 |

OTHER PUBLICATIONS

Chem. Abstracts 76:126530k (Journ. Org. Chem., vol. 37, No. 4, p. 673 (1972)).

*Primary Examiner*—Ethel G. Love
*Attorney, Agent, or Firm*—Sprung Horn Kramer & Woods

[57] ABSTRACT

Benzyl esters of the formula

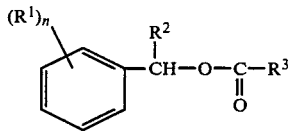

in which
n is 1,2,3,4, or 5,
$R^2$ is hydrogen, $C_{1-4}$-alkyl, cyano or ethynyl,
$R^3$ is the radical of a carboxylic acid customary in pyrethroids or pyrethroid-like compounds, and
at least one $R^1$ is fluoroalkoxy or fluoroalkylmercapto, or two together are fluoromethylene- or fluoroethylene-dioxy, and the others, if present, are hydrogen or various radicals, which possess arthropodicidal properties. Various alcohols, amines, aldehydes, halides, and the like, corresponding to the alcohol moieties of the esters are also synthesized.

3 Claims, No Drawings

COMBATING ARTHROPODS WITH NOVEL BENZYL ESTERS

This is a division of application Ser. No. 288,440, filed July 30, 1981, now U.S. Pat. No. 4,438,275, which is a division of application Ser. No. 30,579, filed Apr. 16, 1979, now U.S. Pat. No. 4,310,540.

The present invention relates to and has for its objects the provision of particular new benzyl esters which possess arthropodical properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It also relates to new intermediate products for the preparation of these active compounds.

Similar active compounds are already known from French Patent Specification No. 2,290,415

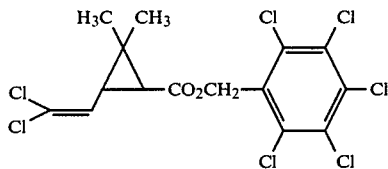

or are present in the commercial product Neopynamin

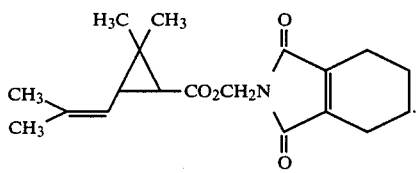

However, these compounds have the disadvantage of too low an activity, above all when low concentrations are applied.

1. The present invention now provides, as new compounds, the benzyl esters of the general formula

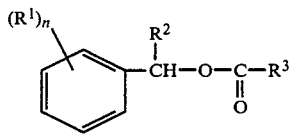

in which
  n represents 1, 2, 3, 4 or 5, the substituents $R^1$ being selected independently of each other when n is 2 or more,
  $R^1$ represents hydrogen, $C_{1-6}$-alkyl, $C_{1-6}$-halogenoalkyl with 3–6 halogen atoms, $C_{1-6}$-alkoxy, $C_{1-6}$-halogenoalkoxy with 1–6 halogen atoms, $C_{1-6}$-alkylmercapto, $C_{1-6}$-halogenoalkylmercapto with 1–6 halogen atoms, halogen, optionally substituted phenyl or optionally substituted phenoxy, or two adjacent radicals $R^1$, together with the adjoining carbon atoms, form an optionally substituted fused-on benzene ring or form a fused-on oxygen-containing heterocyclic five-membered or six-membered ring which is mono- or polysubstituted by fluorine, provided that, in formula I, at least one of the radicals $R^1$ must represent fluoroalkoxy or fluoroalkylmercapto, or two adjacent radicals, together with the adjoining carbon atoms, form an oxygen-containing heterocyclic five-membered or six-membered ring which is mono- or polysubstituted by fluorine,
  $R^2$ represents hydrogen, $C_{1-4}$-alkyl, cyano or ethynyl and
  $R^3$ represents the radical of a carboxylic acid customary in pyrethroids or pyrethroid-like compounds.

2. This invention also provides a process for the preparation of a benzyl ester of the formula (I) in which
  (a) a carbonyl halide of the general formula

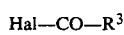

Hal—CO—$R^3$    (II), in which
  $R^3$ has the meaning stated under 1 (above) and
  Hal represents halogen, preferably chlorine, is reacted with a benzyl alcohol of the general formula

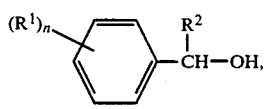

in which $R^1$, n and $R^2$ have the meaning stated under 1 (above), if appropriate in the presence of an acid acceptor and if appropriate in the presence of a solvent, or
  (b) a salt of a carboxylic acid, of the general formula

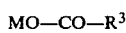

MO—CO—$R^3$    (IV), in which
  M denotes K or Na and
  $R^3$ has the meaning stated under 1 (above), is reacted with a benzyl halide of the general formula

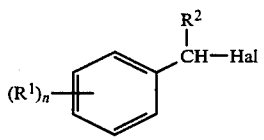

in which
  $R^1$, n and $R^2$ have the meanings stated under 1 (above) and
  Hal denotes chlorine or bromine,
if appropriate in the presence of a solvent and if appropriate in the presence of a quaternary ammonium salt.

3. The new benzyl alcohols of the general formula

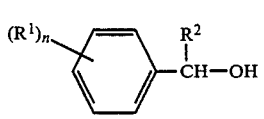

in which $R^1$, $R^2$ and n have the meanings stated under 1 (above), have also been found.

4. It has also been found that a benzyl alcohol of the formula (III) in 3 (above) is obtained when
  (a) an aldehyde of the general formula

  (VI)

in which R¹ and n have the meanings stated under 1 (above), is reduced, in the case where R² in the benzyl alcohol represents hydrogen, or is reacted with HCN, in the case where R² in the benzyl alcohol represents CN, or is reacted with a Grignard compound of the formula

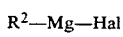  (VII), in which R² represents $C_{1-4}$-alkyl or ethynyl, in the case where R² in the benzyl alcohol represents $C_{1-4}$-alkyl or ethynyl, or (b) when a benzylamine of the general formula

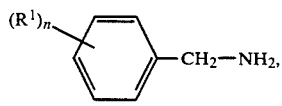  (VIII)

in which R¹ and n have the meanings stated under 1 (above), is reacted with sodium nitrite or potassium nitrite in the presence of an acid, or (c) when a benzyl halide of the general formula

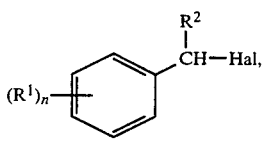  (V)

in which R¹, R², n and Hal have the meanings stated under 2 (above), is saponified with an aqueous base.

5. The new benzyl halides of the general formula

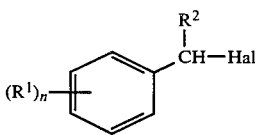  (V)

in which

R² and n have the meanings stated under 4 (above) and each R¹ represents, independently of any other, hydrogen, $C_{1-6}$-alkyl, $C_{1-6}$-halogenoalkyl with 3-6 halogen atoms. $C_{1-6}$-alkoxy, $C_{1-6}$-halogenoalkoxy with 1-6 halogen atoms, $C_{1-6}$-alkylmercapto, $C_{1-6}$-halogenoalkylmercapto with 1-6 halogen atoms, halogen, optionally substituted phenyl and optionally substituted phenoxy, or two adjacent radicals R¹, together with the adjoining carbon atoms, form an optionally substituted fused-on benzene ring or form a fused-on oxygen-containing heterocyclic five-membered or six-membered ring which is mono- or polysubstituted by fluorine, provided that, in this formula, two adjacent radicals R¹, together with the adjoining carbon atoms, must form an oxygen-containing heterocyclic five-membered or six-membered ring which is optionally monosubstituted or polysubstituted by fluorine, have also been found.

6. It has also been found that a benzyl halide of the formula (V) in 5 (above) is obtained when a compound of the general formula

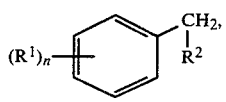  (IX)

in which R¹, R² and n have the meanings stated under 5 (above), is halogenated in the side chain in a manner which is in itself known.

7. The new aldehydes of the general formula

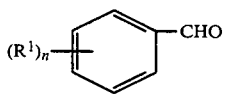  (VI)

in which R¹ and n have the meanings stated under 5 (above), but with the proviso that two adjacent radicals R¹, together with the adjoining carbon atoms, must form an oxygen-containing six-membered ring which is monosubstituted or polysubstituted by fluorine, have also been found.

8. It has also been found that an aldehyde of the formula (VI) in 7 (above) is obtained when, in compounds of the general formula

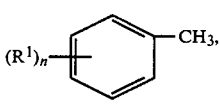  (XI)

in which R¹ and n have the meanings stated under 8 (above), the $CH_3$ group is halogenated to the —CH—$Hal_2$ group in a manner which is in itself known and this group is then saponified in the customary manner to give the aldehyde of the formula (VI).

9. The new benzylamines of the general formula

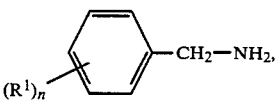  (VIII)

in which R¹ and n have the meanings stated under 1 (above), have also been found.

10. It has also been found that a benzylamine of the formula (VIII) in 9 (above) is obtained when a compound of the general formula

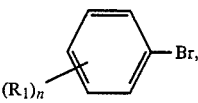  (XII)

in which R¹ and n have the meanings stated under 5 (above), is reacted, in a first stage, with a cyanide salt and the nitrile thereby obtained, of the general formula

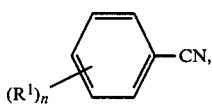 (XIII)

is hydrogenated in a manner which is in itself known.

11. A process has also been found for the preparation of a compound of the formula (XIII), (XI) or (IX), or of a similar compound, characterized in that (a), in the case where two adjacent radicals $R^1$, together with the two adjoining carbon atoms, form an oxygen-containing heterocyclic five-membered ring which is substituted by fluorine, a compound having the general formula

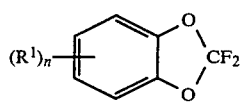 (XIV)

in which
n represents 1, 2, 3 or 4 and
each $R^1$ independently represents hydrogen, $C_{1-6}$-alkyl, trihalogenomethyl, $C_{1-6}$-alkoxy, $C_{1-6}$-halogenoalkoxy with 1-6 halogen atoms, $C_{1-6}$-alkylmercapto, $C_{1-6}$-halogenoalkylmercapto with 1-6 halogen atoms, halogen, optionally substituted phenyl or phenoxy, chlorocarbonyl, chlorosulphonyl or nitro, or two adjacent radicals $R^1$, together with the adjoining carbon atoms, form an optionally substituted fused-on benzene ring,
is obtained when a compound of the general formula

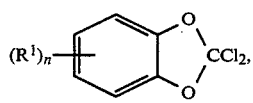 (XV)

in which $R^1$ and n have the meanings stated above, is reacted with anhydrous hydrofluoric acid, or (b), in the case where two adjacent radicals $R^1$, together with the two adjoining carbon atoms, form an oxygen-containing heterocyclic six-membered ring which is substituted by fluorine, a compound having the general formula

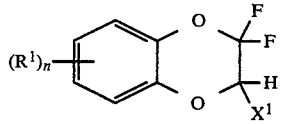 (XVI)

in which
n represents 1, 2, 3 or 4 and
each $R^1$ independently represents hydrogen, $C_{1-6}$-alkyl, $C_{1-6}$-fluoroalkyl with 3-6 fluorine atoms, $C_{1-6}$-alkoxy, $C_{1-6}$-halogenoalkoxy with 1-6 halogen atoms, $C_{1-6}$-alkylmercapto, $C_{1-6}$-halogenoalkylmercapto with 1-6 halogen atoms, $C_{2-6}$-alkenyl, $C_{2-6}$-alkynyl, halogen, optionally substituted phenyl or phenoxy, carboxyl, nitro, cyano or $SO_3H$, or two of the radicals $R^1$ denote a fused-on benzene ring and
$X^1$ represents hydrogen or halogen,
is obtained when a compound of the general formula

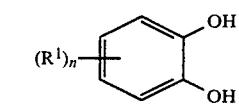 (XVII)

in which $R^1$ and n have the meanings stated above, is reacted with a compound of the general formula

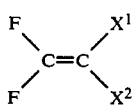 (XVIII)

in which
$X^2$ represents halogen and
$X^1$ represents hydrogen or halogen.

12. The new compounds of the general formula

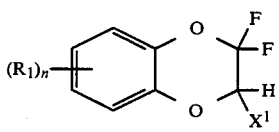 (XVI)

in which $R^1$, n and $X^1$ have the meanings stated under 11(b) (above), have also been found.

The compounds of the formula (I) exhibit good insecticidal properties. Surprisingly, these new active compounds according to the invention exhibit a considerably higher activity than the compounds known from the state of the art.

Preferred compounds of the formula (I) are those in which
n represents 1, 2, 3, 4 or 5,
each $R^1$ independently represents hydrogen, fluorine, chlorine, bromine, trifluoromethyl, methoxy, difluoromethoxy, trifluoromethoxy, tetrafluoroethoxy, hexafluoropropoxy, difluoromethylthio or trifluoromethylthio, or phenyl or phenoxy, either of which may be optionally substituted by halogen or alkoxy, or two adjacent radicals $R^1$, together with the adjoining carbon atoms, form an oxygen-containing five-membered or six-membered ring which is polysubstituted by fluorine, with the proviso that at least one of the radicals $R^1$ should denote fluoroalkoxy or fluoromethylthio, or that two of the radicals $R^1$ should represent $OCF_2O$, $OCF_2CH_2O$ or $OCF_2CHFO$, thereby forming a 5-membered or 6-membered heterocyclic ring with the two adjoining carbon atoms,
$R^2$ represents hydrogen, $C_1$-$C_4$-alkyl, cyano or ethynyl and
$R^3$ represents the radical

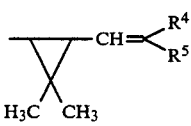

wherein
$R^4$ and $R^5$ are identical or different and represent fluorine, chlorine or bromine, or $R^4$ and $R^5$ both represent methyl, or
$R^3$ represents the radical

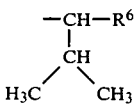

wherein R[6] represents a phenyl ring which is optionally substituted by halogen, alkyl, alkylthio or alkoxy with in each case 1–4 carbon atoms, nitro or methylenedioxy, or represents a naphthyl radical.

Particularly preferred compounds of the formula (I) are those in which each R[1] independently represents hydrogen, chlorine, difluoromethoxy, tetrafluoroethoxy, hexafluoropropoxy or trifluoromethylthio, or two adjacent radicals R[1], together with the adjoining carbon atoms, form a heterocyclic oxygen-containing 5-membered or 6-membered ring, provided that at least one R[1] should denote difluoromethoxy, tetrafluoroethoxy, hexafluoropropoxy or trifluoromethylthio, or that two adjacent radicals R[1] should represent $OCF_2O$, $OCF_2-CH_2O$ or $OCF_2CHFO$ thereby forming a 5-membered or 6-membered heterocyclic ring with the two adjoining carbon atoms, R[2] represents hydrogen or cyano and R[3] represents the radical

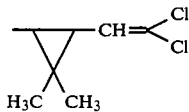

or the radical

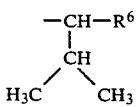

wherein R[6] represents a phenyl ring which is substituted by fluorine, chlorine, bromine, methoxy or methylenedioxy.

Specific compounds of the formula (I) which may be mentioned are the following: 2-difluoromethoxybenzyl 2,2-dimethyl-3-(2′,2′-dichlorovinyl)-cyclopropanecarboxylate, 3-difluoromethoxybenzyl 2,2-dimethyl-3-(2′,2′-dichlorovinyl)-cyclopropanecarboxylate, 2-tetrafluoroethoxybenzyl 2,2-dimethyl-3-(2′,2′-dichlorovinyl)-cyclopropanecarboxylate, 3-tetrafluoroethoxybenzyl 2,2-dimethyl-3-(2′,2′-dichlorovinyl)-cyclopropanecarboxylate, 3-hexafluoropropoxybenzyl 2,2-dimethyl-3-(2′,2′-dichlorovinyl)-cyclopropanecarboxylate, 3-difluoromethoxy-4-chlorobenzyl 2,2-dimethyl-3-(2′,2′-dichlorovinyl)-cyclopropanecarboxylate, 3,4-bis-(difluoromethoxy)-benzyl 2,2-dimethyl-3-(2′,2′-dichlorovinyl)-cyclopropanecarboxylate, 3-trifluoromethylthio-benzyl 2,2-dimethyl-3-(2′,2′-dichlorovinyl)-cyclopropanecarboxylate, 3-trifluoromethoxy-benzyl 2,2-dimethyl-3-(2′,2′-dichlorovinyl)-cyclopropanecarboxylate, 3-difluoromethylthio-benzyl 2,2-dimethyl-3-(2′,2′-dichlorovinyl)-cyclopropanecarboxylate, 3-difluoromethoxy-α-cyanobenzyl 2,2-dimethyl-3-(2′,2′-dichlorovinyl)-cyclopropanecarboxylate, difluoro-3,4-dioxymethylene-benzyl 2,2-dimethyl-3-(2′,2′-dichlorovinyl)-cyclopropanecarboxylate, difluoro-2,3-dioxymethylene-benzyl 2,2-dimethyl-3-(2′,2′-dichlorovinyl)-cyclopropanecarboxylate, difluoro-3,4-dioxymethylene-6-chlorobenzyl 2,2-dimethyl-3-(2′,2′-dichlorovinyl)-cyclopropanecarboxylate, difluoro-3,4-dioxymethylene-6-bromobenzyl 2,2-dimethyl-3-(2′,2′-dichlorovinyl)-cyclopropanecarboxylate, difluoro-3,4-dioxymethylene-2,5,6-trichlorobenzyl 2,2-dimethyl-3-(2′,2′-dichlorovinyl)-cyclopropanecarboxylate, difluoro-3,4-dioxyethylene-benzyl 2,2-dimethyl-3-(2′,2′-dichlorovinyl)-cyclopropanecarboxylate, trifluoro-3,4-dioxyethylene-benzyl 2,2-dimethyl-3-(2′,2′-dichlorovinyl)-cyclopropanecarboxylate, difluoro-3,4-dioxyethylene-6-chlorobenzyl 2,2-dimethyl-3-(2′,2′-dichlorovinyl)-cyclopropanecarboxylate, trifluoro-3,4-dioxyethylene-6-chlorobenzyl 2,2-dimethyl-3-(2′,2′-dichlorovinyl)-cyclopropanecarboxylate, 2-difluoromethoxybenzyl 4′-chlorophenyl-α-isopropylacetate, 3-difluoromethoxybenzyl 4′-chlorophenyl-α-isopropylacetate, 2-tetrafluoroethoxybenzyl 4′-chlorophenyl-α-isopropylacetate, 3-tetrafluoroethoxybenzyl 4′-chlorophenyl-α-isopropylacetate, 3-hexafluoropropoxybenzyl 4′-chlorophenyl-α-isopropylacetate, 3-difluoromethoxy-4-chlorobenzyl 4′-chlorophenyl-α-isopropylacetate, 3,4-bis-(difluoromethoxy)-benzyl 4′-chlorophenyl-α-isopropylacetate, 3-trifluoromethylthio-benzyl 4′-chlorophenyl-α-isopropylacetate, 3-trifluoromethoxy-benzyl 4′-chlorophenyl-α-isopropylacetate, 3-trifluoromethylthio-benzyl 4′-chlorophenyl-α-isopropylacetate, 3-difluoromethoxy-α-cyano-benzyl 4′-chlorophenyl-α-isopropylacetate, difluoro-3,4-dioxymethylenebenzyl 4′-chlorophenyl-α-isopropylacetate, difluoro-2,3-dioxymethylene-benzyl 4′-chlorophenyl-α-isopropylacetate, difluoro-3,4-dioxymethylene-6-chlorobenzyl 4′-chlorophenyl-α-isopropylacetate, difluoro-3,4-dioxymethylene-6-bromobenzyl 4′-chlorophenyl-α-isopropylacetate, difluoro-3,4-dioxymethylene-2,5,6-trichlorobenzyl 4′-chlorophenyl-α-isopropylacetate, difluoro-3,4-dioxyethylene-benzyl 4′-chlorophenyl-α-isopropylacetate, trifluoro-3,4-dioxyethylenebenzyl 4′-chlorophenyl-α-isopropylacetate, difluoro-3,4-dioxyethylene-6-chlorobenzyl 4′-chlorophenyl-α-isopropylacetate and trifluoro-3,4-dioxyethylene-6-chlorobenzyl 4′-chlorophenyl-α-isopropylacetate.

The preparation of the benzyl esters of the formula (I) according to the invention can be represented by the equation which follows:

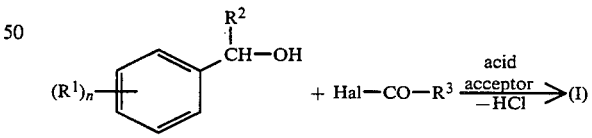

If, for example, 2,2-dimethyl-3-(2′,2′-dichlorovinyl)-cyclopropanecarboxylic acid chloride and difluoro-3,4-methylenedioxybenzyl alcohol are used as starting materials in process variant (a) in 2 (above), the course of the reaction can be represented by the equation which follows:

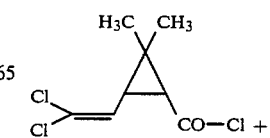

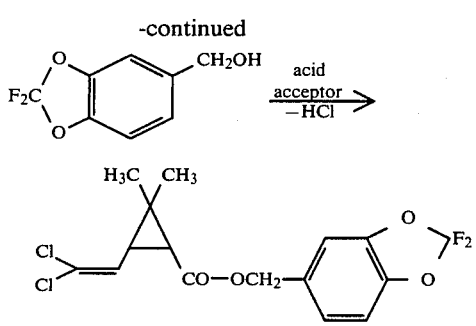

The carbonyl halides of the formula (II) to be used as starting materials are known and can be prepared by the generally customary processes described in the literature (see, for example, DT-OS (German Published Specifications) Nos. 2,365,555; 1,926,433 and 2,231,312).

Specific examples which may be mentioned of the compounds of the formula (II) to be used as starting materials are: 2,2-dimethyl-3-(2',2'-dichlorovinyl)-cyclopropanecarboxylic acid chloride, 2,2-dimethyl-3-(2',2'-dibromovinyl)-cyclopropanecarboxylic acid chloride, 2,2-dimethyl-3-(2',2'-dimethylvinyl)-cyclopropanecarboxylic acid chloride, α-isopropyl-phenylacetic acid chloride, α-isopropyl-4-fluorophenylacetic acid chloride, α-isopropyl-4-chlorophenylaceticacid chloride, α-isopropyl-4-bromophenylacetic acid chloride, α-isopropyl-4-methylphenylacetic acid chloride, α-isopropyl-4-ethylphenylacetic acid chloride, α-isopropyl-4-n-propylphenylacetic acid chloride, α-isopropyl-4-isopropylphenylacetic acid chloride, α-isopropyl-4-methoxyphenylacetic acid chloride, α-isopropyl-4-ethoxyphenylacetic acid chloride, α-isopropyl-4-methylthiophenylacetic acid chloride, α-isopropyl-4-ethylthiophenylacetic acid chloride, α-isopropyl-4-nitrophenylacetic acid chloride, α-isopropyl-3-fluorophenylacetic acid chloride, α-isopropyl-3-bromophenylacetic acid chloride, α-isopropyl-3-chlorophenylacetic acid chloride, α-isopropyl-3-methylphenylacetic acid chloride, α-isopropyl-3-ethylphenylacetic acid chloride, α-isopropyl-3-methoxyphenylacetic acid chloride, α-isopropyl-3-ethoxyphenylacetic acid chloride, α-isopropyl-3-methylthiophenylacetic acid chloride, α-isopropyl-3-ethylthiophenylacetic acid chloride and α-isopropyl-3,4-methylenedioxyphenylacetic acid chloride.

The alcohols of the formula (III) also to be used as starting materials are new.

The new alcohols can be prepared by the processes indicated under 4 (above) (for details see below).

Specific examples which may be mentioned of alcohols of the formula (III) to be used as starting materials are: 2-difluoromethoxy-benzyl alcohol, 3-difluoromethoxy-benzyl alcohol, 3-trifluoromethylthio-benzyl alcohol, 3,4-difluoromethoxy-benzyl alcohol, 3-difluoromethoxy-4-chloro-benzyl alcohol, 3-trifluoromethoxy-benzyl alcohol, 3-trifluoromethylthiobenzyl alcohol, difluoro-3,4-dioxymethylene-benzyl alcohol, 2-difluoromethoxy-α-cyano-benzyl alcohol, 3-difluoromethoxy-α-cyano-benzyl alcohol, 2-trifluoromethylthio-α-cyano-benzyl alcohol, 3,4-difluoromethoxy-α-cyano-benzyl alcohol, 3-difluoromethoxy-4-chloro-α-cyano-benzyl alcohol, 3-trifluoromethoxy-α-cyano-benzyl alcohol, 3-trifluoromethylthio-α-cyano-benzyl alcohol, difluoro-3,4-dioxymethylene-α-cyano-benzyl alcohol, difluoro-3,4-dioxymethylene-α-ethynylbenzyl alcohol, 3-difluoromethoxy-α-ethynyl-benzyl alcohol, 3-difluoromethylthio-benzyl alcohol, 3-difluoromethylthio-α-cyano-benzyl alcohol and 3-tetrafluoroethoxy-benzyl alcohol.

All the customary acid-binding agents can be used as acid acceptors for the preparation of the compounds of the formula (I) from alcohols of the formula (III) and carbonyl halides of the formula (II). Alkali metal carbonates and alcoholates, such as sodium carbonate and potassium carbonate and sodium methylate or ethylate and potassium methylate or ethylate, and furthermore aliphatic, aromatic or heterocyclic amines, for example triethylamine, trimethylamine, dimethylaniline, dimethylbenzylamine and pyridine, have proved particularly suitable.

The reaction temperature can be varied within a substantial range. In general, the reaction is carried out at from 0° to 100° C., preferably at from 15° to 40° C.

In general, the reaction is allowed to proceed under normal pressure. The process for the preparation of the compounds of the formula (I) is preferably carried out also using a suitable solvent or diluent. Virtually any inert organic solvent can be used as the solvent or diluent, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

The starting materials are preferably employed in equimolar amounts for carrying out the process. An excess of one or other of the components provides no substantial advantages. In general, the reactants are brought together in one of the solvents indicated and the mixture is usually stirred for one or more hours at elevated temperature in order to bring the reaction to completion. The reaction mixture is then poured into water and the organic phase is separated off and rinsed with water. After drying, the solvent is distilled off in vacuo.

The new compounds are obtained in the form of oils, some of which cannot be distilled without decomposition, but which can be freed from the last volatile constituents by so-called "incipient distillation", that is to say by prolonged heating to moderately elevated temperatures under reduced pressure, and can be purified in this manner. The refractive index is used for their characterization.

The compounds of the formula (I) are also obtained by reacting the salts of carboxylic acids (IV) with benzyl halides (V):

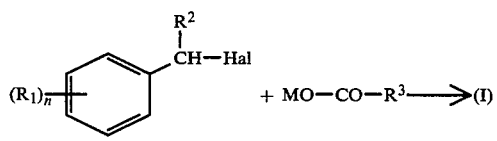

If, for example, the potassium salt of 4-chlorophenylacetic acid (which can appropriately be prepared "in situ" from the acid and KOH) and 3-difluoromethoxy-benzyl bromide are used as starting substances in process variant (b) in 2 (above), the course of the reaction can be represented by the equation which follows:

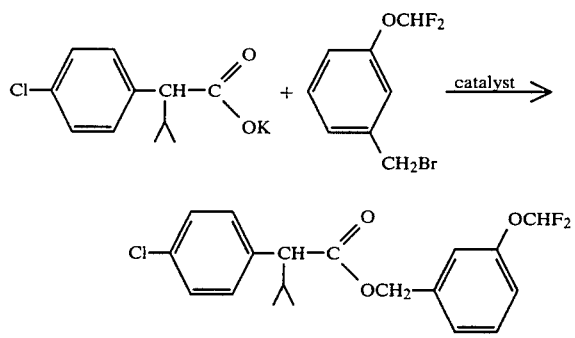

The carboxylic acids of their salts of the formula (IV) to be used as starting materials are known, and the carbonyl halides of the formula (II) are based on them. All the acids and salts on which the acid halides of the formula (II) are based can thus be used for the preparative procedure mentioned above.

Specific examples which may be mentioned are the acids, and their sodium, potassium, calcium or ammonium salts, on which the acid halides listed above are based.

Benzyl halides of the formula (V) used as starting materials are known and can be obtained by processes indicated below.

Specific benzyl halides (V) which may be mentioned are the following: 2-difluoromethoxybenzyl chloride, 3-difluoromethoxybenzyl chloride, 3-difluoromethoxy-4-chlorobenzyl bromide, 3-trifluoromethoxy-benzyl bromide, difluoro-3,4-dioxymethylenebenzyl chloride, difluoro-3,4-dioxymethylenebenzyl bromide, difluoro-3,4-dioxymethylene-6-chlorobenzyl bromide, difluoro-3,4-dioxymethylene-6-bromobenzyl bromide, difluoro-3,4-dioxymethylene-α-cyanobenzyl bromide, difluoro-2,3-dioxymethylene-benzyl chloride, difluoro-2,3-dioxymethylene-benzyl bromide, 3-tetrafluoroethoxy-benzyl chloride, 3-tetrafluoroethoxy-benzyl bromide and difluoro-3,4-dioxymethylene-2,5,6-trichlorobenzyl chloride.

A solvent such as an aromatic, optionally chlorinated hydrocarbon, for example benzene, toluene, xylene, chlorobenzene or dichlorobenzene, is generally used for the preparation of the compounds of the formula (I) from the salts of carboxylic acids, of the formula (IV), and the benzyl halides of the formula (V).

The salts of the carboxylic acids can be employed direct, or can be prepared "in situ" by adding KOH or NaOH in the form of their aqueous solutions or in the powdered form. Quaternary ammonium salts, for example tetrabutylammonium chloride, tetrabutylammonium bromide, benzyltriethylammonium chloride or methyltrioctylammonium chloride, can be used as catalysts.

The reaction temperature can be varied within a substantial range. In general, the reaction is carried out at from 50° to 150° C., preferably at from 30° to 120° C.

The starting materials are preferably employed in equimolar amounts for carrying out the process. An excess of the salt of the acid can be used in order to achieve complete reaction of the benzyl halide. The excess acid can be recovered from the aqueous phase. In most cases, the reaction has ended after 1–5 hours. After cooling the reaction mixture, water is added and the organic phase is separated off and washed until neutral.

The solvent is then distilled off in vacuo and the compounds of the formula (I) are purified as described above.

As already mentioned, the alcohols of the formula (III) are new. They can be prepared by the processes indicated under 4 (above).

In variant 4(a), in the case where $R^2$ in the desired compound of the formula (III) represents hydrogen, the corresponding aldehyde is reduced with hydrogen. This reaction can be represented by the equation which follows:

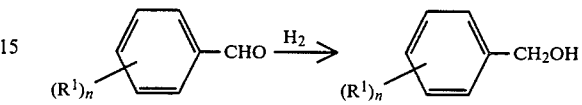

Possible reducing agents are hydrogen in the presence of a catalyst, or complex metal hydrides, for example sodium borohydride or lithium aluminum hydride. The reaction is carried out analogously to known processes (see Organikum, VEB Deutscher Verlag der Wissenschaften, Berlin 1965, 5th edition, page 417; and J. Am. Chem. Soc. 71, 122 (1949); 75, 199 (1953) and 76, 6116 (1954)).

In the case where $R^2$ in the desired compound of the formula (III) represents CN, the corresponding aldehyde is reacted with HCN. This reaction can be represented by the equation which follows:

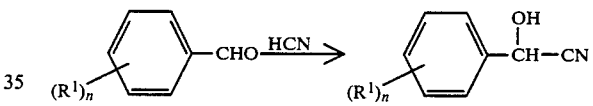

The reaction is carried out analogously to the known processes for the preparation of cyanohydrins (see Organic Syntheses; Coll. Volume I, 336; and Houben-Weyl Volume VIII, page 274 et seq.).

In the case where $R^2$ in the desired compound of the formula (III) represents $C_{1-4}$-alkyl or ethynyl, the corresponding aldehyde is reacted with a Grignard compound of the formula (VII). This reaction can be represented by the equation which follows:

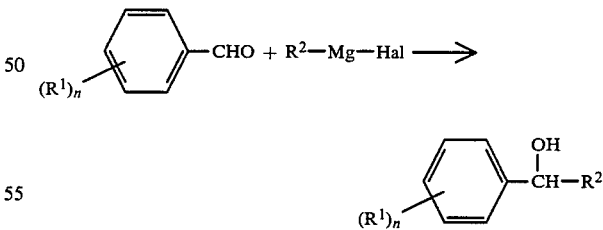

The reaction is carried out analogously to the methods described in, for example, Org. Synth. Coll. Volume IV, page 792.

The Grignard compounds of the formula (VII) are known (see, for example, the literature reference indicated above).

Specific aldehydes of the formula (VI) which may be mentioned are the following: 2-difluoromethoxy-benzaldehyde, 2-trifluoromethylthio-benzaldehyde, 3-difluoromethoxy-benzaldehyde, 3,4-bis-difluoromethoxy-benzaldehyde, 3-difluoromethoxy-4-chloro-benzaldehyde, 3-trifluoromethoxy-benzaldehyde, 3-trifluoromethylthio-benzaldehyde and difluoro-3,4-dioxymethylene-benzaldehyde.

Aldehydes of the formula (VI) are known (see, for example, J. Org. Chem. 37 (673 (1972) and Z. obsc. Chim. 30, 3129 (1960)), and can be prepared by known processes. The difluoromethoxy compounds are obtained, for example, from the corresponding phenols with difluorochloromethane in the presence of bases (see, for example, DOS (German Published Specification) No. 2,150,955 and J. Org. Chem. 25, 2009 (1960)).

Aldehydes of the formula (VI) can be obtained by dihalogenating, preferably dichlorinating, the compounds of the formula (XI) in 8 (above) in the side chain in a manner which is in itself known and saponifying, in a manner which is in itself known, the compounds thus obtained. Specific compounds of the formula (XI) which may be mentioned are the following: trifluoro-3,4-dioxyethylenetoluene, difluoro-3,4-dioxyethylenetoluene, trifluoro-2,3-dioxyethylenetoluene and trifluoro-3,4-dioxyethylene-6-chloro-toluene.

In variant 4(b), benzylamines of the formula (VIII) are reacted with nitrous acid in the presence of an acid, for example acetic acid. This reaction can be represented by the equation which follows:

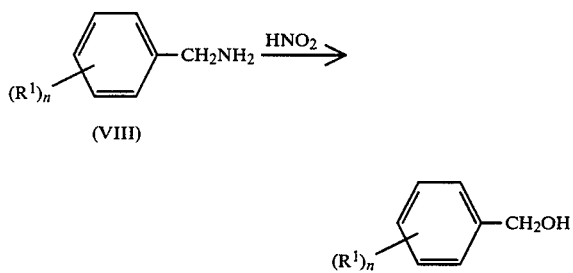

(VIII)

The benzylamines of the formula (VIII) used in this reaction are new, and are obtained by reducing the corresponding nitriles with hydrogen analogously to known processes (Houben-Weyl, Volume XI/1, page 577). The nitriles are obtained, for example, by reacting the corresponding bromine compounds with copper(I) cyanide analogously to known processes (Houben-Weyl, Volume VIII, page 302). If, for example, two radicals $R^1$ together denote $OCF_2O$ and $R^2$ represents hydrogen, the entire course of the reaction can be represented by the equation which follows:

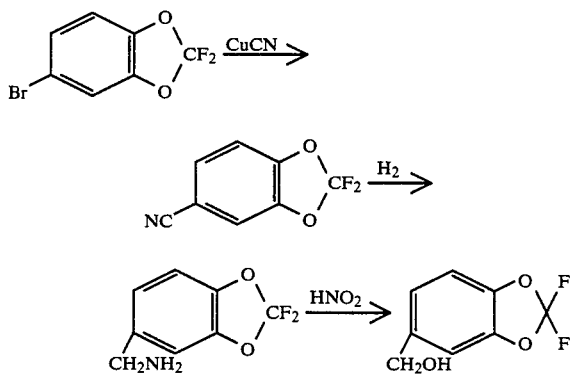

In variant, 4(c), the benzyl halides of the formula (V) are saponified. This reaction can be represented by the equation which follows:

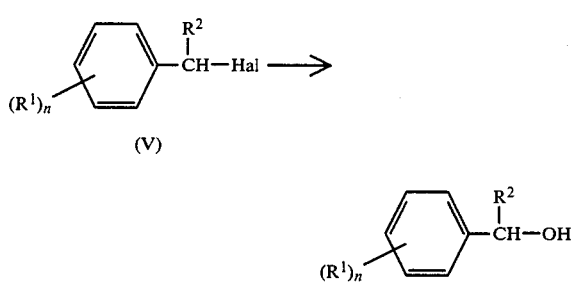

(V)

The saponification is carried out in a manner which is in itself known using aqueous bases, for example NaOH, KOH or alkali metal carbonates, such as $Na_2CO_3$ or $K_2CO_3$.

Benzyl halides of the formula (V) used in processes 2(b) and 4(c) (above) are obtainable, for example, as indicated under 6 (above) by halogenating, in particular brominating or chlorinating, compounds of the general formula

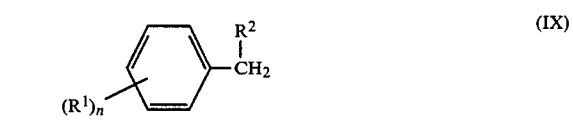

(IX)

by methods which are known in principle.

Examples of possible halogenating agents are chlorine or N-chloro- or N-bromo-succinimide.

The chlorination or bromination of the above-mentioned compounds to give the corresponding benzyl chlorides or bromides is carried out in a manner which is in itself known under free radical conditions using chlorine, N-chlorosuccinimide or N-bromo-succinimide in a solvent, for example methylene chloride, chloroform, carbon tetrachloride, chlorobenzene or o-difluorobenzene, preferably at elevated temperature.

Specific starting compounds of the formula (IX) which may be mentioned are: 2-difluoromethoxytoluene, 2-difluoromethoxy-6-chloro-toluene, 3-difluoromethoxy-toluene, 3-difluoromethoxy-4-chloro-toluene, 3-difluoromethoxy-6-chlorotoluene, 3,4-difluoromethoxy-toluene, 2,3-difluoromethoxytoluene, difluoro-3,4-dioxymethylene-toluene, difluoro-3,4-dioxymethylene-6-chloro-toluene, difluoro-2,3-dioxymethylenetoluene, trifluoro-3,4-dioxyethylene-toluene, difluoro-3,4-dioxyethylenetoluene, trifluoro-2,3-dioxyethylenetoluene, difluoro-2,3-dioxyethylenetoluene, 3-trifluoromethylthiotoluene, 1-n-propyl-difluoro-3,4-methylenedioxy-benzene, 3-tetrafluoroethoxy-toluene and 3-hexafluoropropoxy-toluene. Starting compounds mentioned for the processes in 6, 8 and 10 (above) can be obtained, for example, by the process indicated under 11(a) (above).

The compounds of the formula (XIV) in which one radical $R^1$ denotes $C_{1-6}$-alkyl and the other radicals $R^1$ represent identical or different radicals from the group comprising hydrogen, $C_{1-6}$-alkoxy, $C_{1-6}$-halogenoalkoxy with 1-6 halogen atoms, $C_{1-6}$-alkylmercapto, $C_{1-6}$-halogenoalkylmercapto with 1-6 halogen atoms, halogen and optionally substituted phenyl, or two adjacent radicals, together with the adjoining carbon atoms, form an optionally substituted fused-on benzene ring, are preferred.

The compounds (XIV) in which one radical $R^1$ denotes methyl and the other radicals $R^1$ represent identical or different radicals from the group comprising hydrogen and halogen are very particularly preferred.

Specific examples which may be mentioned are: difluoro-3,4-dioxymethylene-toluene, difluoro-3,4-dioxymethylene-6-fluoro-toluene, difluoro-3,4-dioxymethylene-6-chlorotoluene, difluoro-3,4-dioxymethylene-6-bromo-toluene, difluoro-3,4-dioxymethylene-2,5,6-trichlorotoluene, difluoro-3,4-dioxymethylene-2,5,6-trifluorotoluene and difluoro-2,3-dioxymethylene-toluene.

It is known to obtain 2,2-difluorobenzodioxoles from 2,2-dichlorobenzodioxoles by reaction with antimony trifluoride (Z. obsc. Khim. 30 (1960) No. 9, 3129–3132). However, this is not a process which can be utilized industrially, since antimony trifluoride is rather expensive and, in the method mentioned, is converted into aqueous solutions of antimony chlorides which cannot be recovered without effort.

It has now been found that compounds of the formula (XIV) in 11 (above) are obtained when compounds of the formula

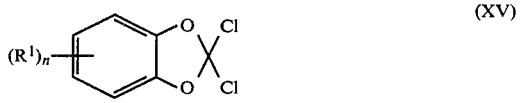

(XV)

in which $R^1$ and n have the meanings indicated in 11(a) (above) are reacted with anhydrous hydrofluoric acid.

Starting substances of the formula (XV) can be prepared from the corresponding benzodioxoles (J. Chem. Soc. 93, 566 (1908)), the corresponding catechol carbonates (Chem. Ber. 96, 1382 (1963)) or the corresponding catechol orthoformates (Chem. Ber. 94, 544 (1961)) by reaction with $PCl_5$.

Starting substances of the formula (XV) in which $R^1$ represents identical or different radicals from the group comprising hydrogen, $C_{1-4}$-alkyl, such as methyl, ethyl, n-propyl, i-propyl or t-butyl, trichloromethyl, fluorine, chlorine, bromine, phenyl which is optionally substituted by halogen or $C_{1-4}$-alkyl, for example methyl, chlorocarbonyl, chlorosulphonyl and nitro, or two adjacent radicals, together with the adjoining carbon atoms, form a fused-on benzene ring, are preferably employed.

Specific examples of the starting substances of the formula (XV) which may be mentioned are: 2,2-dichlorobenzodioxole, 4-methyl-2,2-dichlorobenzodioxole, 5-methyl-2,2-dichlorobenzodioxole, 5-ethyl-2,2-dichlorobenzodioxole, 5-propyl-2,2-dichlorobenzodioxole, 5-isopropyl-2,2-dichlorobenzodioxole, 4-methyl-2,2,5,6-tetrachlorobenzodioxole, 5-methyl-2,2,6-trichlorobenzodioxole, 5-methyl-2,2,4,6-tetrachlorobenzodioxole, 5-propyl-2,2,6-trichlorobenzodioxole, 5-methyl-6-bromo-2,2-dichlorobenzodioxole, 5-fluoro-2,2-dichlorobenzodioxole, 5-bromo-2,2-dichlorobenzodioxole, 2,2,5-trichlorobenzodioxole, 4-phenyl-2,2-dichlorobenzodioxole, 5-phenyl-2,2-dichlorobenzodioxole, 4-methoxy-2,2-dichlorobenzodioxole, 5-methoxy-2,2-dichlorobenzodioxole, 4-phenoxy-2,2-dichlorobenzodioxole, 5-(3'-methyl)-phenoxy-2,2-dichlorobenzodioxole, 4-(4'-nitro)-phenoxy-2,2-dichlorobenzodioxole, 5-tert.-butyl-2,2-dichlorobenzodioxole, 5-chloro-6-nitro-2,2-dichlorobenzodioxole, 2,2,4,6-tetrachlorobenzodioxole, 2,2,5,6-tetrachlorobenzodioxole, 5-methyl-2,2,4,6,7-pentachloro-benzodioxole, 4-chlorocarbonyl-2,2-dichlorobenzodioxole, 5-chlorocarbonyl-2,2-dichlorobenzodioxole, 5-nitro-2,2-dichlorobenzodioxole, 2,2-dichloronaphtho-2,3-dioxole and 2,2-dichloro-naphtho-1,2-dioxole.

The reaction in the process variant 11(a) can be carried out at temperatures from −20° C. to 80° C., and preferably at temperatures from 0° C. to 40° C.

The hydrofluoric acid must be employed in at least stoichiometric amounts, and in fact an excess is generally favorable. Thus, the amount of hydrofluoric acid is preferably twice to three times the stoichiometric amount, but the excess can be greater. The reaction can be carried out in the presence of solvents and also without solvents. Possible solvents are, quite generally, inert, aprotic liquids. For example, methylene chloride, trichlorofluoromethane, carbon tetrachloride, chlorobenzene or nitrobenzene can successfully be used. The amount of solvent is not important for the process according to the invention. Thus, the reaction is preferably carried out without a solvent if the starting materials are liquid.

In general, the reaction is carried out under normal pressure, but it can also be carried out under increased pressure.

The process according to the invention can, for example, be carried out as follows:

The required amount of anhydrous hydrofluoric acid is initially introduced into the reaction vessel at about −10° C. and the 2,2-dichlorobenzodioxole is added dropwise, while stirring. The temperature is chosen so that evolution of hydrogen chloride starts immediately, and the gas formed is passed, via a reflux condenser, to a receiver, where it is condensed or neutralized. When the addition has ended, the temperature can be increased slightly. The mixture is stirred until the evolution of gas has ended, and the excess hydrofluoric acid is then distilled off under normal pressure or reduced pressure. The reaction product remains as the residue and can then be purified, for example by distillation.

Compared with known processes for the preparation of 2,2-difluorobenzodioxoles, the process according to the invention has the advantage that it is simple to carry out and gives rise to no ecologically unacceptable effluents. Furthermore, the excess fluorinating agent can be recovered in a simple manner and employed again in the reaction.

The other starting compounds mentioned in the processes in 6, 8 and 10 (above) and similar compounds can be obtained, for example, by the process indicated under 11(b) (above).

In this process, catechols of the general formula

(XVII)

in which $R^1$ and n have the meanings indicated under 11(b) (above), are reacted with compounds of the general formula

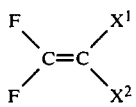

in which
X² represents halogen, preferably F or Cl, and
X¹ represents hydrogen or halogen, preferably F or Cl,
in the presence of a base.

If 4-methylcatechol and trifluorochloroethylene are used as starting materials, the course of the reaction can be represented by the equation which follows:

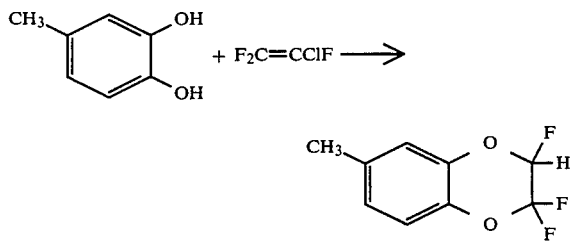

Catechols of the formula (XVII) in which $(R^1)_n$ represents identical or different radicals from the group comprising hydrogen, $C_{1-4}$-alkyl, in particular methyl, ethyl or t-butyl, fluorine, chlorine, bromine, phenyl which is optionally substituted by $C_{1-4}$-alkyl, in particular methyl, or halogen, in particular chlorine or bromine, carboxyl (COOH), nitro, CN or $SO_3H$, or two of the radicals $R^1$, together with the adjoining carbon atoms, form a fused-on benzene ring, may be mentioned as preferred starting materials.

Specific compounds of the formula (XVII) which may be mentioned are the following: catechol, 3-methylcatechol, 4-methylcatechol, 4-tert.-butyl-catechol, 4-chloro-catechol, 4-bromo-catechol, 3,5-dichlorocatechol, 4,5-dichlorocatechol, 3,4,5-trichlorocatechol, tetrachlorocatechol, 3,4-dihydroxybiphenyl, 2,3-naphthalenediole, 4-methyl-5-chlorocatechol, 4-methyl-3,5,6-trichlorocatechol, 2,3-dihydroxy-benzoic acid, 3,4-dihydroxy-sulphonic acid, 4-nitrocatechol, 4-cyanocatechol and 2,3-dihydroxyterephthalic acid.

Specific examples of compounds of the formula (XVIII) which may be mentioned are: chlorotrifluoroethylene, tetrafluoroethylene, bromotrifluoroethylene, chlorodifluoroethylene, 1,1-dichloro-2,2-difluoroethylene and bromodifluoroethylene.

Chlorotrifluoroethylene and chlorodifluoroethylene are particularly preferred.

Suitable bases are, in particular, the hydroxides of the alkali metals and alkaline earth metals, but also the carbonates of these metals. The amount of base can vary between one and more than three moles per mole of pyrocatechol. An excess has a favorable effect. The reaction can be carried out at temperatures from 20° C. to 150° C., particularly preferably in the range from 80° to 120° C. A polar liquid is used as the solvent. Examples of solvents which have proved suitable are: dimethylsulphoxide, dimethylformamide and tetramethylenesulphone, and also ethers, such as dioxane, or diglyme. Tetramethylenesulphone is preferred.

The reaction is carried out under normal pressure or under increased pressure, in order to prevent the fluorinated ethylenes escaping if they do not react immediately when metered in. In general, the reaction is carried out between 1 and 30 bars, preferably between 1 and 15 bars.

The process according to the invention can be carried out under 1 bar as follows:

The catechol, dissolved in the solvent is initially introduced into the reaction vessel, the base is added and the mixture is warmed to the reaction temperature (for example 100° C.), while stirring. After about half an hour, the fluorinated ethylene is then passed in at the rate at which it is taken up by the reaction solution. Towards the end of the reaction, non-consumed olefin passes through and can be recycled again into the reaction. If the reaction is carried out under increased pressure, the catechols, bases and solvents are initially introduced into a pressure vessel, the mixture is warmed to the reaction temperature and the ethylenes of the formula (XVIII) are then pumped in at a rate such that the desired pressure is established.

When the reaction has ended, the mixture is worked up either by fractional distillation or by diluting with water and separating off the reaction product.

As already mentioned, the compounds of the formula (I) exhibit insecticidal activity.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratoroioides, Melanoplus differentialis* and *Schistocera gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporari-* orum, *Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents.

In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dye-stuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredients a compound of the present invention in admixture with a solid or liquefied gaseous diluent or carrier or in admixture with a liquid diluent or carrier containing a surface-active agent.

The present invention also provides a method of combating arthropods, especially insects, which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects by the application to said animals of a compound according to the present invention, in admixture with a diluent or carrier.

Preparation of the novel compounds is shown in the following illustrative examples:

EXAMPLE 1

(A) Preparation of the starting substances (i) 2-Difluoromethoxybenzyl alcohol 51.5 g (0.3 mol) of 2-difluoromethoxybenzaldehyde were dissolved in 100 ml of ethanol, and 6.25 g of sodium borohydride in 100 ml of ethanol were added dropwise at 25°–35° C. The mixture was then further stirred until room temperature was reached and was diluted with water and acidified with 25% strength $H_2SO_4$. After extracting twice with methylene chloride, the organic phase was dried and the solvent was distilled off. A colorless oil was obtained in almost quantitative yield and, ater some time, solidified. The 2-difluoromethoxybenzyl alcohol melted at 42° C.

(ii) 2- and 3-Trifluoromethylthiobenzyl alcohol

These were obtained from 2- and 3-trifluoromethyl-thiobenzaldehyde analogously to (i).

(iii) 2-Difluoromethoxy-α-cyano-benzyl alcohol 7.2 g of potassium cyanide were dissolved in 30 ml of water and 6 ml of ethanol, while cooling. 16 g of 2-difluoromethoxybenzaldehyde were then added at 0°–5° C., while cooling. After subsequently stirring the mixture between 0° and 10° C. for 20 minutes, a mixture of 7 ml of concentrated $H_2SO_4$ and 18 ml of water was added dropwise. The mixture was subsequently stirred for a further 2 hours and was thereby allowed to come to room temperature. After extracting twice with methylene chloride, the organic phase was dried and the solvent was distilled off. 2-Difluoromethoxy-α-cyano-benzyl alcohol was obtained as a colorless oil, the structure of which was confirmed by a nuclear magnetic resonance spectrum. The yield was virtually quantitative.

(iv) Analogously to (iii), 2-trifluoromethylthio-α-cyano-benzyl alcohol was obtained from 2-trifluoromethylthio-benzaldehyde and difluoro-3,4-dioxymethylene-α-cyano-benzyl alcohol was obtained from difluoro-3,4-dioxymethylene-benzaldehyde.

(v) Analogously to (i), difluoro-3,4-dioxymethylene-benzyl alcohol was obtained from difluoro-3,4-dioxymethylenebenzaldehyde by reduction with sodium borohydride. The NMR spectrum (in $CDCl_3$) confirmed the structure: 3.7 ppm (s, OH); 4.6 ppm (s, $CH_2$); and 7.0 ppm and 7.05 ppm (3. aromatic H).

(vi) Difluoro-3,4-methylenedioxy-toluene 200 ml of HF (anhydrous) were initially introduced into the reaction vessel at 0° C. and 190 g of dichloro-3,4-methylenedioxytoluene (see J. Chem. Soc. 93, 563) were added dropwise. When the evolution of hydrogen chloride had ended, the mixture was warmed to 20° C. and stirred for 1 hour and excess hydrofluoric acid was then distilled off under reduced pressure. Difluoro-3,4-methylenedioxytoluene boiled at 74°–78° C./52 mm ($n_d^{20}$=1.492).

(vii) 1-n-Propyl-difluoro-3,4-methylenedioxy-benzene was obtained analogously to the above instructions. Boiling point=80°/15 mm Hg ($n_D^{20}$=1.4540).

(viii) Difluoro-3,4-methylenedioxy-benzyl bromide 172 g (1 mol) of difluoro-3,4-methylenedioxytoluene, 180 g of N-bromosuccinimide and a pinch of azobisisobutyronitrile were mixed with 1,000 ml of $CCl_4$ and the mixture was heated to the boil for 5 hours. After cooling, it was filtered, the residue was rinsed with a little $CCl_4$ and the filtrate was distilled. 180 g (72% of theory) of difluoro-3,4-methylenedioxy-benzyl bromide of boiling point=180°–111° C./15 mm Hg and refractive index $n_D^{20}$=1.518 were obtained.

(ix) 1-Bromo-1-(difluoro-3,4-methylenedioxy)-phenylpropane of boiling point 70°–73° C./0.3 mm Hg were obtained analogously to (viii).

(x) Difluoro-3,4-methylenedioxy-6-chloro-benzyl bromide 14 g of chlorine were passed into a solution of 34.4 g (0.2 mol) of difluoro-3,4-methylenedioxy-toluene in 40 ml of methylene chloride at −10° C. to −5° C. The mixture was allowed to come to room temperature and was fractionated under a waterpump vacuum. 31 g of difluoro-3,4-methylene-dioxy-6-chloro-toluene of boiling point 80°–84°/15 mm Hg were obtained and were dissolved in 150 ml of carbon tetrachloride. After adding 33 g of N-bromo-succinimide and a pinch of azibisisobutyronitrile, the mixture was heated to the boil for 5 hours. 30 g of difluoro-3,4-methylenedioxy-6-chloro-benzyl bromide of boiling point 74°–75° C./0.25 mm Hg and refractive index $n_D^{20}$ of 1.5334 were obtained.

(xi) Trifluoro-3,4-dioxyethylene-benzyl bromide 124 g of 4-methylpyrocatechol were dissolved in 300 ml of tetramethylene sulphone, and 110 g of KOH were added. 170 g of trifluorochloroethylene were then passed in at 100° to 110° C. After cooling, the mixture was distilled over a column, under a waterpump vacuum. 132 g of trifluoro-3,4-dioxyethylene-toluene of boiling point 70°–72° C./12 mm Hg and $n_D^{20}$ of 1.4565 were obtained.

50 g of the product were brominated with 50 g of N-bromosuccinimide in 150 ml of CCl$_4$ analogously to the above instructions (8 hours under reflux). The trifluoro-3,4-dioxyethylene-benzyl bromide boiled at 123°–124° C./13 mm Hg; refractive index $n_D^{20}$=1.5165.

(xii) 4-Methyl-2,2-difluorobenzodioxole 200 ml of HF were initially introduced into the reaction vessel at 0° C. and 100 g of 4-methyl-2,2-dichlorobenzodioxole were added dropwise. When the evolution of hydrogen chloride had ended, the mixture was warmed further to 20° C., and subsequently stirred for 1 hour and the excess hydrofluoric acid was then distilled off under reduced pressure. The 4-methyl-2,2-difluorobenzodioxole had a boiling point of 42°–45° C./11 mm Hg ($n_D^{20}$: 1.4515).

4-Bromomethyl-2,2-difluorobenzodioxole boiled at 93°–96° C./10 mm Hg ($n_D^{20}$=1.5115).

(xiii) 5-Propyl-2,2-difluorobenzodioxole 100 ml of anhydrous hydrofluoric acid were initially introduced into the reaction vessel at −2° C. and 110 g of 5-propyl-2,2-dichlorobenzodioxole were then added dropwise. After carrying out the reaction analogously to xv(a), infra, 67 g of 5-propyl-2,2-difluorobenzodioxole with a boiling point ef 80°–83° C./15 mm Hg ($n_D^{20}$: 1.4540) were obtained.

(xiv) Difluoromethylene-3,4-dioxybenzoic acid 100 ml of anhydrous hydrofluoric acid were initially introduced into the reaction vessel at −3° C. and 55 g of 5-chlorocarbonyl-2,2-dichlorobenzodioxole were then added dropwise. When the addition had ended, the mixture was warmed further to 20° C. and stirred until the evolution of hydrogen chloride had ended. The excess hydrofluoric acid was then distilled off and the residue was stirred into 200 ml of 5% strength sodium hydroxide solution. The solution was filtered and then acidified with hydrochloric acid. The difluoromethylene-3,4-dioxybenzoic acid which had precipitated was filtered off and dried. 35 g of acid with a melting point of 153°–154° C. were obtained.

(xv) 2,2-Difluorobenzodioxole (a) 600 g of anhydrous hydrofluoric acid were initially introduced into a V$_4$A reaction vessel with a stirrer, reflux condenser and dropping funnel at −10° C. 612 g of 2,2-dichlorobenzodioxole were then added dropwise in the course of about 2 hours, with exclusion of moisture. Evolution of hydrogen chloride started immediately. The gas was passed through a delivery tube from the reflux condenser into a receiver containing water and was absorbed. When the addition had ended, the temperature was increased to 18°–20° C. and the mixture was subsequently stirred for a further 1 hour until the evolution of gas had ended. The excess hydrofluoric acid was now distilled off over a column and collected in a cooled receiver. 394 g of 2,2-difluorobenzodioxole ($n_D^{20}$: 1.4430) were then distilled over under a pressure of 100 mm with a boiling point of 65°–70° C. The yield was 78% of theory.

(b) A solution of 150 g of 2,2-dichlorobenzodioxole in 200 ml of methylene chloride was added dropwise to 200 ml of anhydrous hydrofluoric acid in a V$_4$A reaction vessel, while stirring. The reaction started immediately at 0° C. The mixture was allowed to react completely at 0° C., the temperature was then increased to 20° C. and the mixture was stirred for a further hour.

The excess hydrofluoric acid and the solvent were then distilled off under reduced pressure and the 2,2-difluorobenzodioxole was subsequently distilled over. 85 g of product were obtained, which corresponded to 68% of theory.

(xvi) 2,2-Difluoro-5-chloro-benzodioxole was obtained analogously to xv(a). Boiling point=57° C./14 mm Hg ($n_D^{20}$=1.4712), (xvii) 2,2-Difluoro-1,4-benzodioxene 110 g of pyrocatechol were initially introduced into 300 ml of tetramethylene sulphone, together with 70 g of potassium hydroxide, and the mixture was heated to 100° C. in the course of 30 minutes, while stirring. 140 g of 1,1-difluoro-2-chloroethylene were passed in at a temperature of 110°–110° C. (time: about 3 hours). The product was then distilled over a small column under 15 mm Hg into a well cooled receiver. During this procedure, it was heated up to an internal temperature of 100° C. The contents of the receiver were transferred to a separating funnel and the organic phase was separated off from the aqueous phase. 112 g ($\dot{=}$65% of theory) of 2,2-difluoro-1,4-benzodioxene which had the refractive index $n_D^{20}$ of 1.4802 and which, according to analysis by gas chromatography, was pure, were obtained.

(xviii) 6-Methyl-2,2,3-trifluoro-1,4-benzodioxene 124 g of 4-methylpyrocatechol were initially introduced into 300 ml of tetramethylene sulphone, together with 110 g of potassium hydroxide, at 110° C. 170 g of trifluorochloroethylene were then passed in in the course of 4 hours. The mixture was then distilled over a column under 15 mm Hg, the distillate being removed up to a transition temperature of 85° C. After separating off the aqueous phase in the receiver, the product was again distilled. 133 g (=65% of theory) of 6-methyl-2,2,3-trifluoro-1,4-benzodioxene were obtained at a boiling point 70°–72° C./12 mm Hg ($n_D^{20}$: 1.4565).

(xix) 2,2,3-Trifluoro-1,4-benzodioxene 220 g of pyrocatechol and 130 g of sodium hydroxide were initially introduced into 600 ml of tetramethylene sulphone at 95°–105° C. and 330 g of trifluorochloroethylene were passed in at this temperature, whilst stirring. The mixture was then distilled over a column under 15 mm Hg and a fraction of boiling point 20° to 60° C./15 mm Hg was collected in a well-cooled receiver. After the H$_2$O phase had been separated off, 332 g of pure 2,2,3-trifluoro-1,4-benzodioxene of boiling point 54°–5° C./12 mm Hg and $n_D^{20}$ of 1.4525 remained, in a yield of 87% of theory.

(xx) 2,2,3-Trifluoro-5,7,8-trichloro-6-chloromethyl-1,4-benzodioxene 60 g of 6-methyl-2,2,3-trifluoro-benzodioxene were initially introduced into the reaction vessel with 1 g FeCl$_3$ at 25° C. and chlorine was passed into this mixture. The temperature was allowed to rise slowly to 80° C. and chlorination was continued until saturation took place. After a short preliminary run 71 g of product with a melting point of 84°–86° C. were distilled at 120°–125° C./0.15 mm.

(xxi) 3-difluoromethoxy-2,4,5,6-tetrachloro-benzyl-chloride 100 g of difluoromethoxy-toluene were chlorinated with 2 g of iodine at 25°–30° C. After passing in approximately 150 g of chlorine the reaction mixture solidified and 50 ml of CH$_2$Cl$_2$ were added and chlorination continued at 40° C. until saturation took place. After the solvent had been distilled off a solid product remained which was introduced into a filter and subsequently washed with cyclohexane. 140 g of 3-difluoromethoxytetrachlorotoluene were obtained (melting-point 86°–88° C.). This was dissolved in 250 ml of o-dichlorobenzene and chlorinated with about 150 g of chlorine at 175°–185° C. under ulta-violet irradiation. Following distillation (b.p.=140°–142° C./1.2 mm) 112 g of 3-difluoromethoxy-2,4,5,6-tetrachlorobenzyl chloride were obtained.

(xxii) 4,6,7-Trichloro-2,2-difluoro-5-chloromethyl-benzodioxole 162 g of 5-methyl-2,2-difluoro-benzodioxole were initially introduced into the reaction vessel with 1 g Fe S at 10° C. and chlorine was passed in. When the chlorine absorption decreased, the temperature was increased slowly until saturation was reached at 70° C. After a preliminary running 210 g of 5-chloromethyltrichloro-2,2-difluorobenzodioxole of b.w.=104°–105° C./0.3 mm were obtained. Melting point 48°–50° C.

(xxiii) 3-trifluoromethoxy-benzyl alcohol was obtained by the reduction of 3-trifluoromethoxy-benzoyl-fluoride with NaBH$_4$ in dioxane B.p.=95°–97° C./15 mm: $n_D^W$=1.4485. 3-chlorodifluoromethoxybenzyl alcohol: b.p.=123° C./14 mm: $n_D^{20}$=1.480 was obtained analogously from 3-chlorodifluoromethoxy benzoylfluoride.

(xxiv) 2,2,3-trifluoro-6-hydroxy-cyano-methyl-1,4-benzodioxene 40 g of hexamethylene tetramine were heated in 50 ml water to 100° C. and 40 g of 6-chloromethyl-2,2,3-trifluorobenzodioxene were added dropwise. After one hour at 100° C. 100 ml of H$_2$O and 100 ml of concentrated hydrochloric acid were added and the mixture was stirred for 2 hours at 100° C. By means of subsequent steam distillation 20 g of 6-formyl-2,2,3-trifluoro-1,4-benzodioxene were obtained with a b.p.=119°–120° C./15 mm; $n_D^{20}$=1.5001), which was converted analogously to Example (iii) with KCN into cyanohydrin.

(xxv) 3-Trifluoromethoxy-benzoyl fluoride were initially introduced with 5 g Fe S under reflux (167° C.) into the reaction vessel and chlorine was passed in. The chlorine absorption was poor at the beginning, but increased at the same rate as the temperature. At 180° C. chlorination was carried to saturation.

This raw mixture was reduced in 500 ml of dioxene at 20° C. with 65 g of sodium boron hydride and extracted with CH$_2$Cl$_2$ (following hydrolysis) and distilled. At b.p.$_{15}$=148°–152° C. a fraction was obtained which, after standing at 20° C., partly crystallized. The crystals were filtered off with suction and were washed with hexane, melting point 50°–52° C.; according to H$^1$NMR-spectrum 5-trifluoromethoxy-2,3,4-trichloro-benzyl alcohol was obtained.

After distilling off the hexane an oil remained 80% of which, according to H$^1$-NMR consisted of 3-trifluoromethoxy-2,5,6-trichlorobenzyl alcohol.

The second fraction in the distillation (b.p.$_{13}$: 170°–5° C., 76°–8° C.) consisted of 3-trifluoromethoxy-2,4,5,6-tetrachlorobenzyl alcohol.

(B) 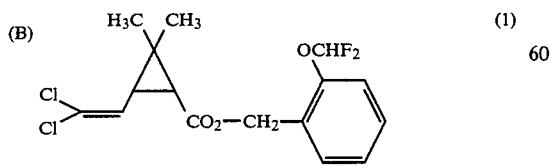 (1)

6.09 g (0.035 mol) of 2-difluoromethoxybenzyl alcohol and 3.5 g (0.035 mol) of triethylamine were dissolved in 50 ml of toluene and the solution was added dropwise to a mixture of 7.95 g (0.35 mol) of 2,2-dimethyl-3-(2′,2′-dichloro-vinyl)-cyclopropanecarboxylic acid chloride in 100 ml of toluene at 20°–25° C. The reaction mixture was subsequently stirred at room temperature for 3 hours and poured into 150 ml of water, the toluene phase was filtered off, washed with 100 ml of water and dried with sodium sulphate and the toluene was distilled off in vacuo. Last residues of solvent were removed by incipient distillation at a bath temperature of 60° C./0.2 to 1.0 mm Hg. 10.9 g (81% of theory) of 2-difluoromethoxybenzyl 2,2-dimethyl-3-(2′,2′-dichlorovinyl)-cyclopropanecarboxylate were obtained as a viscous oil with the refractive index $n_D^{20}$=1.5190.

The following compounds were obtained analogously:

| Compound | Formula | Refractive index $n_D^{20}$ |
|---|---|---|
| 2 | CH$_3$ CH$_3$, Cl, Cl, CO$_2$CH(CN)—C$_6$H$_4$—OCHF$_2$ | 1.5191 |
| 3 | H$_3$C CH$_3$, Cl, Cl, CO$_2$CH$_2$—C$_6$H$_3$—O—CF$_2$—O | 1.5070 |
| 4 | H$_3$C CH$_3$, Cl, Cl, CO$_2$CH$_2$—C$_6$H$_4$—SCF$_3$ | 1.5260 |
| 5 | H$_3$C CH$_3$, Cl, Cl, CO$_2$CH(CN)—C$_6$H$_4$—SCF$_3$ | 1.5240 |
| 6 | H$_3$C CH$_3$, Br, Br, CO$_2$CH$_2$—C$_6$H$_3$—O—CF$_2$—O | 1.5230 |
| 7 | Cl—C$_6$H$_4$—CH(C(CH$_3$)$_2$H$_3$C)—CO$_2$CH$_2$—C$_6$H$_3$—O—CF$_2$—O | 1.5170 |
| 8 | H$_3$C CH$_3$, Cl, Cl, CO$_2$CH$_2$—C$_6$H$_4$—SCF$_2$ | 1.5154 |

-continued

| Compound | Formula | Refractive index $n_D^{20}$ |
|---|---|---|
| 9 | 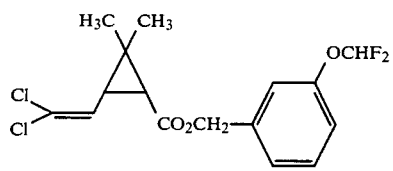 | 1.5062 |

EXAMPLE 2

(10)

H3C CH3
Cl\
  C=CH—△—CO2CH2—C6H4—OCHF2
Cl/

6.81 g (0.03 mol) of 3-difluoromethoxy-benzyl bromide and 6.27 g (0.03 mol) of 2,2-dimethyl-3-(2',2'-dichlorovinyl)-cyclopropanecarboxylic acid were dissolved in 150 ml of toluene, 0.5 g of tetrabutylammonium bromide and 2 g of powdered KOH (industrial product, 87% pure) were added and the mixture was heated to the boil for 2–3 hours. After cooling, the reaction mixture was poured into 150 ml of water, the toluene phase was separated off, washed with 100 ml of water and dried with sodium sulphate and the toluene was distilled off in vacuo. Last residues of solvent were removed by incipient distillation at a bath temperature of 60°–80° C./0.2 to 1 mm Hg. 8.3 g (78% of theory) of 3-difluoromethoxy-benzyl 2,2-dimethyl-3-(2',2'-dichlorovinyl)-cyclopropanecarboxylate were obtained as a viscous oil with the refractive index $n_D^{20}=1.5110$.

EXAMPLE 3

The procedure followed was as in Example 2, but 5.74 g (0.03 mol) of 3-difluoromethoxy-benzyl chloride were used instead of 3-difluoromethoxybenzyl bromide. After boiling the mixture under reflux for 4 hours, 7.9 g (74% of theory) of 3-difluoromethoxy-benzyl 2,2-dimethyl-3-(2',2'-dichlorovinyl)-cyclopropanecarboxylate were obtained.

The following compounds were obtained analogously to Example 2 or 3:

| Compound | Formula | Refractive index $n_D^{20}$ |
|---|---|---|
| 12 | Cl2C=CH—△(H3C,CH3)—CO2CH2—C6H3(OCHF2)(Cl) | 1.5200 |
| 13 | Cl2C=CH—△(H3C,CH3)—CO2—CH2—C6H3(OCHF2)(Cl) | 1.5210 |
| 14 | Cl2C=CH—△(H3C,CH3)—CO2CH2—C6H3(OCHF2)(OCHF2) | 1.4960 |
| 15 | Cl2C=CH—△(H3C,CH3)—CO2CH2—C6H3(Cl)(OCHF2O) | 1.5110 |
| 16 | Cl2C=CH—△(H3C,CH3)—CO2CH2—C6H3(OCF2O) | 1.5080 |

-continued

| Compound | Formula | Refractive index $n_D^{20}$ |
|---|---|---|
| 17 | H₃C, CH₃ cyclopropane with Br₂C=CH and CO₂CH₂-phenyl-OCHF₂ (meta) | 1.5280 |
| 18 | H₃C, CH₃ cyclopropane with Cl₂C=CH and CO₂CH₂-phenyl-OCHF₂, Cl | 1.5154 |
| 19 | 4-Cl-phenyl-CH(CH(CH₃)₂)-CO₂CH(CN)-phenyl-OCF₂O (3,4-methylenedioxy-difluoro) | 1.5150 |
| 20 | 4-F-phenyl-CH(CH(CH₃)₂)-CO₂CH₂-phenyl-OCHF₂ | 1.5136 |
| 21 | 4-Br-phenyl-CH(CH(CH₃)₂)-CO₂CH₂-phenyl-OCF₂O | 1.5205 |
| 22 | 3,4-methylenedioxyphenyl-CH(CH(CH₃)₂)-CO₂CH₂-phenyl-OCF₂O | 1.4992 |
| 23 | H₃C, CH₃ cyclopropane with Cl₂C=CH and CO₂CH₂-phenyl-OCF₂CHFCF₃ | 1.4780 |
| 24 | H₃C, CH₃ cyclopropane with Cl₂C=CH and CO₂CH₂-phenyl-OCF₂CHF₂ | 1.4950 |
| 25 | H₃C, CH₃ cyclopropane with Cl₂C=CH and CO₂CH(CH₂CH₃)-phenyl-OCF₂O | 1.5164 |

-continued

| Compound | Formula | Refractive index $n_D^{20}$ |
|---|---|---|
| 26 | [structure: dichlorovinyl dimethylcyclopropane carboxylate-CH2-phenyl with OCHF-CHF2 dioxole] | 1.5090 |
| 27 | [structure: 4-Cl-phenyl-CH(CH(CH3)2)-CO2CH2-phenyl with OCHF-CHF2 dioxole] | 1.5149 |
| 28 | [structure: 4-Cl-phenyl-CH(CH(CH3)2)-CO2-CH2-phenyl-OCHF2] | 1.5193 |
| 29 | [structure: dichlorovinyl dimethylcyclopropane-CO2CH2-trichlorophenyl with OCHF-CHF2 dioxole] | 1,543 |
| 30 | [structure: dichlorovinyl dimethylcyclopropane-CO2CH2-trichlorophenyl-OCHF2] | 1,546 |
| 31 | [structure: dichlorovinyl dimethylcyclopropane-CO2CH2-trichlorophenyl with O-CF2-O dioxole] | 1.538 |

The following additional compounds were obtained analogously to Example 1:

| Compound | Formula | Refractive Index $n_D^{20}$ |
|---|---|---|
| 32 | [structure: dichlorovinyl dimethylcyclopropane-CO2CH2-phenyl-OCF3] | 1.493 |
| 33 | [structure: dichlorovinyl dimethylcyclopropane-CO2CH2-dichlorophenyl-OCF3] | 1.532 |

-continued

| Compound | Formula | Refractive Index $n_D^{20}$ |
|---|---|---|
| 34 | (cyclopropane with H₃C, CH₃, CCl=CHCl substituents)—CO₂CH₂—(phenyl with OCF₃, Cl, Cl, Cl) | 1.530 |
| 35 | (cyclopropane with H₃C, CH₃, CCl=CHCl substituents)—CO₂CH₂—(phenyl with Cl, OCF₃, Cl, Cl) | 1.538 |
| 36 | (cyclopropane with H₃C, CH₃, CCl=CHCl substituents)—CO₂CH₂—(phenyl with OCF₂Cl) | 1.512 |
| 37 | (cyclopropane with H₃C, CH₃, CCl=CHCl substituents)—CO₂CH(CN)—(phenyl with O—CHF—CF₂—O linkage) | 1.517 |

The insecticidal activity of the compounds of this invention is illustrated by the following biotest Examples.

In these Examples, the compounds according to the present invention are each identified by the number (given in brackets) of the corresponding preparative Example, which will be found later in this specification.

EXAMPLE 4

$LT_{100}$ test for Diptera
Test insects: *Musca domestica* (resistant)
Number of test insects: 20
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was continuously checked. The time which was necessary for a 100% knockdown effect was determined.

In this test, for example, the following compounds showed a superior action compared to the prior art: (3), (4), (6), (15), (8), (10), (1), (12), (13) and (17).

EXAMPLE 5

$LT_{100}$ test for Diptera
Test insects: *Aedes aegypti*
Number of test insects: 20
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was continuously checked. The time which was necessary for a 100% knockdown effect was determined.

In this test, for example, the following compounds showed a superior action compared to the prior art: (1), (3), (4), (6), (8), (10), (12), (13), (15), (17) and (2).

EXAMPLE 6

Mosquito larvae test
Test insects: *Aedes aegypti* larvae (4th stage)
Solvent: 99 parts by weight of acetone
Emulsifier: 1 part by weight of benzylhydroxydiphenyl polyglycol ether To produce a suitable preparation, the active compound was dissolved, at a rate of 2 g per liter, in the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage.

In this test, for example, the following compounds showed a superior action compared to the prior art: (3), (4), (6), (15), (8), (10), (1), (12), (13) and (17).

EXAMPLE 7

Laphygma test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified periods of time, the destruction in % was determined.

In this test, for example, the following compounds showed a superior activity compared to the prior art: (4), (8), (1), (10), (17), (13), (12), (3), (6) and (15).

It will be appreciated that the instant specification and examples are set forth by way of illustration and not limitation, and that various modifications and changes may be made without departing from the spirit and scope of the present invention.

What is claimed is:

1. A compound of the formula

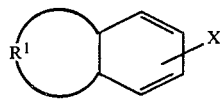

in which
R$^1$ is a 2,2-difluoroethylenedioxy or 2,2,3-trifluoroethylenedioxy radical, and
X is

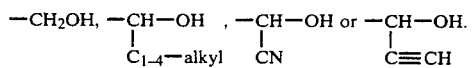

2. A compound according to claim 1, of the formula

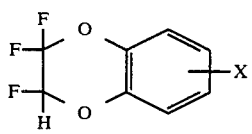

3. A compound according to claim 1, of the formula

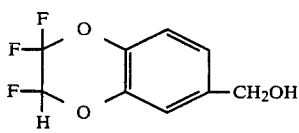

* * * * *